United States Patent
Guo et al.

(10) Patent No.: US 10,391,238 B2
(45) Date of Patent: Aug. 27, 2019

(54) INTELLIGENT INFUSION SYSTEM AND INFUSION METHOD USING INTELLIGENT INFUSION SYSTEM

(71) Applicants: BOE TECHNOLOGY GROUP CO., LTD., Beijing (CN); BEIJING BOE OPTOELECTRONICS TECHNOLOGY CO., LTD., Beijing (CN)

(72) Inventors: Baolei Guo, Beijing (CN); Gang Ci, Beijing (CN); Xiao Ma, Beijing (CN); Huanyu Wang, Beijing (CN); Na An, Beijing (CN); Hao Wu, Beijing (CN); Xinfeng Gong, Beijing (CN)

(73) Assignees: BOE TECHNOLOGY GROUP CO., LTD., Beijing (CN); BEIJING BOE OPTOELECTRONICS TECHNOLOGY CO., LTD., Beijing (CN)

( * ) Notice: Subject to any disclaimer, the term of this patent is extended or adjusted under 35 U.S.C. 154(b) by 178 days.

(21) Appl. No.: 15/537,947

(22) PCT Filed: May 16, 2016

(86) PCT No.: PCT/CN2016/082208
§ 371 (c)(1),
(2) Date: Jun. 20, 2017

(87) PCT Pub. No.: WO2017/152493
PCT Pub. Date: Sep. 14, 2017

(65) Prior Publication Data
US 2018/0099085 A1    Apr. 12, 2018

(30) Foreign Application Priority Data
Mar. 10, 2016 (CN) .......................... 2016 1 0136086

(51) Int. Cl.
*A61M 5/142* (2006.01)
*A61M 5/168* (2006.01)
(Continued)

(52) U.S. Cl.
CPC .............. *A61M 5/142* (2013.01); *A61M 5/14* (2013.01); *A61M 5/168* (2013.01);
(Continued)

(58) Field of Classification Search
CPC .. A61M 5/142; A61M 5/172; A61M 5/16836; A61M 5/16886; A61M 5/168;
(Continued)

(56) References Cited

U.S. PATENT DOCUMENTS 7,922,688 B2 * 4/2011 Bodduluri ............... A61M 5/20
604/156
9,364,171 B2 7/2016 Harris et al.
(Continued)

FOREIGN PATENT DOCUMENTS

CN    101171046 A    4/2008
CN    104000637 A    8/2014
(Continued)

OTHER PUBLICATIONS

Second Office Action for Chinese Patent Application No. 20160136086.X dated Dec. 5, 2018.
(Continued)

*Primary Examiner* — Jaime Figueroa
(74) *Attorney, Agent, or Firm* — Calfee, Halter & Griswold LLP (57) ABSTRACT

An intelligent infusion system and an infusion method using an intelligent infusion system are disclosed. The system includes: a positioning device configured to determine a coordinate origin; an imaging device configured to capture a first image of an object in a first state and a second image (Continued)

of the object in a second state; a processing device configured to compare the first image and the second image to determine one or more objects to be processed and image data of each object to be processed; a calculation device configured to select a target object, select a first position on the target object, and determine coordinates of the first position based on the coordinate origin; and a control device configured to control a robotic arm to reach a liquid input region, and control the robotic arm to move a infusion needle to the coordinates of the first position for liquid infusion.

20 Claims, 4 Drawing Sheets (51) Int. Cl.
*A61M 5/14* (2006.01)
*A61M 5/172* (2006.01)
*A61B 34/20* (2016.01)
*A61B 5/15* (2006.01)

(52) U.S. Cl.
CPC .... *A61M 5/16836* (2013.01); *A61M 5/16886* (2013.01); *A61M 5/172* (2013.01); *A61B 5/15003* (2013.01); *A61B 5/150748* (2013.01); *A61B 2034/2055* (2016.02); *A61M 5/1685* (2013.01); *A61M 5/16854* (2013.01); *A61M 2005/14208* (2013.01); *A61M 2205/3523* (2013.01); *A61M 2205/50* (2013.01)

(58) Field of Classification Search
CPC ............... A61M 5/14; A61M 2205/50; A61M 2205/3523; A61M 2005/14208; A61M 5/16854; A61M 5/1685; A61B 5/15003; A61B 5/150748; A61B 2034/2055
USPC .................................................. 700/245, 259
See application file for complete search history.

(56) References Cited

U.S. PATENT DOCUMENTS

| 2003/0171670 | A1* | 9/2003 | Gumb ................ A61B 17/3403 600/411 |
| 2008/0275396 | A1 | 11/2008 | Neerken et al. |
| 2010/0010505 | A1* | 1/2010 | Herlihy ................... A61B 90/11 606/130 |
| 2010/0274202 | A1* | 10/2010 | Hyde ................. A61B 10/0283 604/272 |
| 2012/0190981 | A1 | 7/2012 | Harris et al. |
| 2013/0123798 | A1* | 5/2013 | Tsao ....................... A61B 90/10 606/130 |
| 2013/0345718 | A1* | 12/2013 | Crawford ............. A61B 17/025 606/130 |
| 2014/0142422 | A1* | 5/2014 | Manzke ................ A61B 8/0841 600/424 |
| 2015/0335531 | A1* | 11/2015 | Yuyama ..................... A61J 1/20 141/18 |
| 2015/0339442 | A1* | 11/2015 | Oleynik ................ G06F 19/324 705/3 |
| 2016/0136052 | A1* | 5/2016 | Koike ....................... A61J 1/16 141/94 |
| 2016/0177298 | A1* | 6/2016 | Green ................... A61K 9/0048 424/133.1 |
| 2016/0256093 | A1 | 9/2016 | Harris et al. |

FOREIGN PATENT DOCUMENTS

| CN | 104248790 A | 12/2014 |
| CN | 105056351 A | 11/2015 |
| CN | 105327429 A | 2/2016 |
| CN | 105536093 A | 5/2016 |
| CN | 205494538 U | 8/2016 |
| EP | 1888152 A2 | 2/2008 |
| EP | 2654593 A1 | 10/2013 |
| JP | 2012035010 A | 2/2012 |
| WO | 2006120619 A2 | 11/2006 |
| WO | 2012088471 A1 | 6/2012 |

OTHER PUBLICATIONS

International Search Report for PCT Application No. PCT/CN2016/082208 dated Nov. 10, 2016.

* cited by examiner

INTELLIGENT INFUSION SYSTEM AND INFUSION METHOD USING INTELLIGENT INFUSION SYSTEM

CROSS-REFERENCE TO RELATED APPLICATIONS

This application is based upon International Application No. PCT/CN2016/082208, filed on May 16, 2016, which is based upon and claims priority of Chinese Patent Application No. 201610136086.X filed on Mar. 10, 2016, which is hereby incorporated by reference in its entirety as part of this application.

TECHNICAL FIELD

The present disclosure relates to the field of medical devices, and more particularly to an intelligent infusion system and an infusion method using the intelligent infusion system.

BACKGROUND

Currently, the existing infusion equipment is usually dependent on a manual operation of a medical staff. Because the experience of the medical staff is different and the diameter sizes of the blood vessels of different patients are different, there may be many failures in the infusion of the infusion equipment. The existing infusion equipment will increase the patient's pain, such that patients have aversion to medical institutions.

In addition, the medical model is developing rapidly with comprehensive medical institutions as mainstream, community medical institutions as assistant, and family health care, recovery and prevention as supplement. More and more patients need to use a variety of household medical supplies for continuous treatment after leaving the hospital, which has brought great business opportunities to the field of home medical equipments. Therefore, the family medical supplies market which focuses on home medical equipments with the main function of health care and conditioning and family medical supplies with the main function of assistant treatment chronic diseases has broad prospects.

Moreover, with the increasing development of Internet health care, the demand for professional medical services at home is growing. In general, the existing infusion equipments must be operated by a medical practitioner with professional experience, and the general patients can not be infused by themselves or by their family. As a result, the existing infusion equipments have increased the cost of medical care and reduced the efficiency of medical care.

It should be noted that, information disclosed in the above background portion is provided only for better understanding of the background of the present disclosure, and thus it may contain information that does not form the prior art known by those skilled in the art.

SUMMARY

The present disclosure provides an intelligent system and an infusion method using the intelligent infusion system.

According to an aspect of the present disclosure, an intelligent infusion system is provided, which comprises:

a positioning device configured to determine a coordinate origin;

an imaging device configured to capture a first image of an object to be detected in a first state and a second image of the object to be detected in a second state;

a processing device configured to compare the first image and the second image to determine one or more objects to be processed and image data of each object to be processed;

a calculation device configured to select a target object from the one or more objects to be processed, select a first position on the target object according to image data of the target object and determine coordinates of the first position based on the coordinate origin; and a control device configured to control a robotic arm to reach a liquid input region and control the robotic arm to move a infusion needle to the coordinates of the first position for liquid infusion.

According to another aspect of the present disclosure, an infusion method using an intelligent infusion system is provided, which comprises:

determining a coordinate origin;

capturing a first image of an object to be detected in a first state and a second image of the object to be detected in a second state;

comparing the first image and the second image to determine one or more objects to be processed and image data of each object to be processed;

selecting a target object from the one or more objects to be processed and selecting a first position on the target object according to image data of the target object and determining coordinates of the first position based on the coordinate origin; and controlling a robotic arm to reach a liquid input region, and controlling the robotic arm to move a infusion needle to the coordinates of the first position for liquid infusion.

It is to be understood that both the foregoing general description and the following detailed description are exemplary and explanatory only and are not restrictive of the invention, as claimed.

This section provides a summary of various implementations or examples of the technology described in the disclosure, and is not a comprehensive disclosure of the full scope or all features of the disclosed technology.

BRIEF DESCRIPTION OF THE DRAWINGS

The exemplary implementations of the present disclosure may be more fully understood by reference to the following accompanying drawings, in which.

DETAILED DESCRIPTION

Exemplary implementations of the present disclosure will now be described with reference to the accompanying drawings, however, the present disclosure may be embodied in many different forms and is not limited to the embodiments described herein. Rather, these embodiments are provided to disclose the present disclosure in detail and completely, and to fully convey the scope of the present disclosure to those skilled in the art. The terms in the exemplary implementations shown in the accompanying drawings are not to be limited to the present disclosure. In the drawings, the same units/elements use the same reference numerals.

Unless otherwise indicated, the terms (comprising technical terms) used herein have a common understanding of those skilled in the art. In addition, it is to be understood that terms that are defined by commonly used dictionaries should be understood to have the same meaning as the context of their related fields and should not be understood in an idealized or too formal sense.

Figure 1:
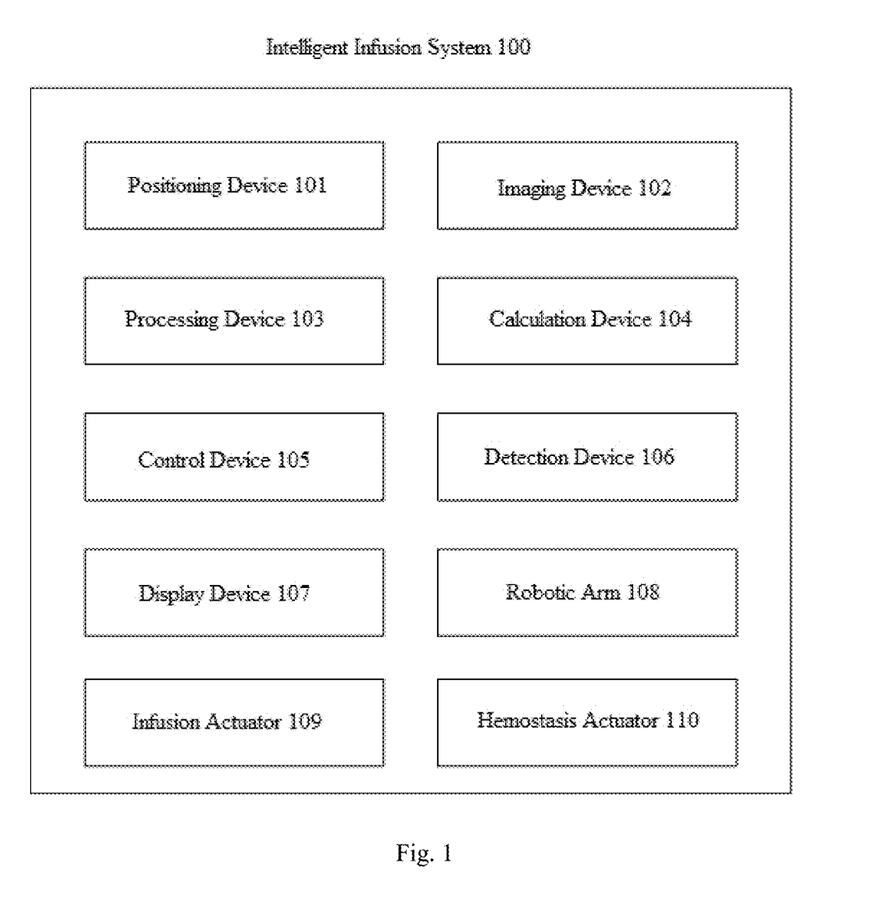
FIG. 1 shows a schematic structural view of an intelligent infusion system according to an implementation of the present disclosure.

FIG. 1 shows a schematic structural view of an intelligent infusion system 100 according to an implementation of the present disclosure. As shown in FIG. 1, the intelligent infusion system 100 comprises but is not limited to a positioning device 101, an imaging device 102, a processing device 103, a calculation device 104, a control device 105, a detection device 106, a display device 107, one or more robotic arms 108, an infusion actuator 109 and a hemostasis actuator 110. In one embodiment, the intelligent infusion system 100 firstly compares and analyzes image data according to an image processing technology to determine vascular distribution of a skin surface of a target object, and then calculates information on a diameter size of a blood vessel according to the image data. Further, the intelligent infusion system 100 sets the initial origin coordinates of the image data and confirms the optimal positional coordinates of the blood vessel for infusion based on the initial origin coordinates. Then, the intelligent infusion system 100 adjusts an angle and a direction of an infusion needle being used for infusion according to the direction and the diameter size of the blood vessel, and then performs an action of inserting the needle accordingly. In one embodiment, the angle of the infusion needle being used for infusion is an angle between the infusion needle and a back of a hand. Generally, when the infusion is performed, the back of a user's hand is in a horizontal state. In one embodiment, the direction of the infusion needle being used for infusion is a relationship between a projection of the infusion needle on a plane where the back of the hand is located and an extension direction of the blood vessel. That is, the direction of the infusion needle being used for infusion needs to be consistent with the extension direction of the blood vessel. In one embodiment, the intelligent infusion system 100 performs the above operations based on calculation and control of a central processing unit CPU.

In addition, the intelligent infusion system 100 can monitor a remaining amount of liquid in the infusion apparatus in real time, and withdraw the infusion needle from the target object when it is determined that the remaining amount of liquid in the infusion apparatus is less than a threshold. In one embodiment, after the infusion needle is withdrawn from the target object, the intelligent infusion system 100 determines the coordinates of the hemostatic position based on the coordinates of the position where the needle is inserted, and sprays cold analgesic sprays for hemostasis at the coordinates of the hemostatic position. When the image data is analyzed based on the image processing technique to determine that the bleeding is stopped, the intelligent infusion system 100 performs a reset operation, for example, resetting the robotic arm.

In one embodiment, the intelligent infusion system 100 may be a miniaturized, intelligent, and networked terminal system or device. The intelligent infusion system 100 can be disposed at home, allowing the user to complete an operation for simple infusion of saline independently. Also, the intelligent infusion system 100 can complete the treatment tasks of infusion at home.

In one embodiment, the positioning device 101 is configured to determine a coordinate origin. The coordinate origin is a reference for determining the coordinates of multiple locations used by a range of infusion treatments for an intelligent infusion system 100. For example, when the intelligent infusion system 100 acquires one or more images of an object to be detected (e.g., a hand of a person who needs the infusion, usually the back of the hand), the same coordinate origin is determined in one or more images. Also, the coordinate origin is used as a reference for determining a number of locations to be used later.

In one embodiment, the imaging device 102 is used to capture pictures of the object to be detected in different states and to capture images of different magnified or reduced degrees. For example, when determining one or more treatment objects (e.g., one or more blood vessels) on the object to be detected, the imaging device 102 captures a first image of the object to be detected in a first state and a second image of the object to be detected in a second state. Usually, the first state is a relaxed state of the object to be detected, and the second state is a tightened state of the object to be detected. For example, the first state is the state in which the hand of the person to be infused is relaxed and laid flat, and the second state is the state in which the person to be infused clenches his fist. It is to be understood that when the object to be detected is in the first state and the second state, the blood vessel exhibits a different effect in the images due to shrinkage or relaxation. In the present disclosure, according to such case that the display effect is different, the image data of one or more blood vessels on the back of the hand is determined, that is, the image data of one or more objects to be processed is determined. Herein, the image data comprises information such as a position, a linear shape, a diameter size and the like of the blood vessel.

In one embodiment, the imaging device 102 is also configured to capture a magnified image. For example, when the intelligent infusion system 100 is used for the liquid infusion, it is usually necessary to obtain a magnified image at the input location to achieve a more accurate liquid infusion. In addition, after the intelligent infusion system 100 completes the liquid infusion, it is usually necessary to perform an operation of stopping bleeding. In the operation of stopping bleeding, the imaging device 102 needs to obtain a magnified image centered on the liquid infusion point (i.e., the second position to be described below) to determine the sprayed location of the hemostatic drug and determine whether hemostasis is achieved after spraying the hemostatic drug. For example, the imaging device 102 continuously acquires a plurality of magnified images centered on the liquid infusion point and determines whether or not hemostasis is achieved by comparing the plurality of magnified images. In one embodiment, when comparing the plurality of magnified images, if swelling occurs at the liquid infusion point or there is a spread of the bleeding point, it is determined that hemostasis is not achieved; otherwise, it is determined that hemostasis has been achieved. In one embodiment, the imaging device 102 can obtain a plurality of magnified images centered on the liquid infusion point after a period of time has elapsed since the liquid infusion is completed, and then it is possible to determine whether hemostasis is achieved by determining whether swelling or a spread of the bleeding point is present at the infusion point. In one embodiment, the above period of time can be any reasonable time. In one embodiment, the imaging device 102 may be a variety of image acquisition devices, such as a camera.

In one embodiment, the processing device 103 compares the first image and the second image to determine one or more objects to be processed and image data of each object to be processed. In particular, the processing device 103 determines one or more objects to be processed and determines a linear shape and a diameter size of each object to be processed by comparing a color change of the first image and the second image. The processing device 103 analyzes and determines the number of the objects to be processed on the object to be detected based on the comparison of the first image and the second image. That is, the number of blood vessels on hand is determined. After one or more objects to be processed are determined, the processing device 103 also determines the image data for each object to be processed. Herein, the image data comprises information such as a position, a linear shape, a diameter size and the like of the blood vessel.

In one embodiment, the calculation device 104 selects a target object from the one or more objects to be processed. The calculation device 104 selects a target object from the one or more objects to be processed according to image data of each object to be processed. That is, the calculation device 104 selects the blood vessel best suited for the liquid infusion from one or more vessels to be used as the target object according to the information such as a position, a linear shape, a diameter size and the like of each blood vessel. In one embodiment, the calculation device 104 selects the target object from one or more objects to be processed by referring to medical data or by image determination. In one embodiment, the calculation device 104 may also select the target object from one or more objects to be processed in a manner that combines medical data with image determination. Then, the calculation device 104 selects a first position on the target object based on the image data of the target object and determines the coordinates of the first position based on the coordinate origin. That is, after the target object is determined, the calculation device 104 also selects the first position suitable for the liquid infusion on the blood vessel according to the information such as the linear shape, the diameter size and the like of the blood vessel. For example, the first position suitable for the liquid infusion may be a location where the diameter size of the blood vessel is larger, the location of the blood vessel closest to the skin surface, or the location suitable for the liquid infusion obtained based on medical statistics.

In one embodiment, the calculation device 104 further calculates a second position based on the first position. According to a preferred implementation of the present disclosure, when the liquid infusion is performed, the infusion needle is first placed on the first position. Herein, the first position is at a certain distance from the point where the infusion needle is being used for the liquid infusion, and the second position is a precise position where the infusion needle being used for the liquid infusion contacts the skin. Generally, when the liquid infusion is performed, the infusion needle is firstly moved to the first position, and the infusion needle is then moved to the second position near the first position by a more sophisticated instrument to carry out the liquid infusion at the second position. In one embodiment, the calculation device 104 further calculates a third position based on the second position. Herein, the third position is a center position where the hemostatic actuator (described later) sprays the cold analgesic sprays after the liquid infusion is completed. That is, the cold analgesic sprays are sprayed at the third position as a center. Herein, the third position is near the second position, such that the second position (the position where the infusion needle contacts the skin) can be completely covered by the cold analgesic sprays when the hemostasis actuator sprays the cold analgesic sprays on the third position. When the hemostasis actuator performs a hemostatic operation, the cold analgesic sprays sprayed on the back of the hand has a fixed radius range centered at the third position. In one embodiment, the intelligent infusion system 100 may be provided with any reasonable fixed radius range. In one embodiment, when the hemostasis actuator performs a hemostatic operation, the spraying of the cold analgesic sprays has a suitable spraying angle such that the cold analgesic sprays can cover a fixed radius range centered on the third position.

In one embodiment, the control device 105 is configured to control the robotic arm to reach a liquid input region, and control the robotic arm to move the infusion needle to the coordinates of the first position for liquid infusion. Typically, one or more robotic arms 108 are not in the liquid input region when not in use. When the liquid infusion is to be performed, the control device 105 generates first control information and sends the first control information to one or more robotic arms 108, such that the one or more robotic arms 108 reach the liquid input region. Herein, after the one or more robotic arms 108 reach the liquid input region, the liquid infusion and hemostasis functions can be done respectively or separately, as described in detail below.

In one embodiment, the detection device 106 is configured to detect a remaining amount of liquid in an infusion apparatus. Typically, when the remaining amount of liquid in the infusion apparatus is below a threshold, for example less than 5 ml, the liquid infusion should be stopped and the infusion needle should be withdrawn from the target object. It is to be understood that one skilled in the art may set the threshold to any reasonable value. In addition, the detection device 106 is also used to detect an infusion flow rate, a blood flow rate, a heart frequency and other parameters.

In one embodiment, the display device 107 is configured to display one or more of the remaining amount of liquid in the infusion apparatus, the infusion flow rate, the blood flow rate and the heart frequency. The display device 107 may be any type of display device, and will not be repeated herein. The display device 107 can display the remaining amount of liquid in the infusion apparatus, the infusion flow rate, the blood flow rate and the heart frequency in real time, such that the user can know about the relevant information in time.

In one embodiment, one or more robotic arms 108 are used to perform the liquid infusion and hemostasis. According to one implementation, the intelligent infusion system 100 comprises one robotic arm 108, and the infusion actuator and the hemostasis actuator are installed at an end of the robotic arm. Herein, the infusion actuator performs the liquid infusion, the hemostasis actuator performs a hemostatic operation, and the infusion actuator and the hemostasis actuator will be described in detail below. According to another implementation, the intelligent infusion system 100 comprises a plurality of robotic arms 108. Take two robotic arms 108 as an example, the infusion actuator is installed at an end of a first robotic arm, and the hemostasis actuator is installed at an end of a second robotic arm.

In one embodiment, the robotic arm 108 is controlled by the control device 105 to reach or leave the liquid input region. Also, the robotic arm 108 is moved to the first position and the third position described as above under the control of the control device 105.

In one embodiment, the infusion actuator 109 is installed at an end of the robotic arm and used to perform the liquid infusion by using the infusion needle. In particular, the control device 105 generates second control information and sends the second control information to the infusion actuator 109. The infusion actuator 109 moves the infusion needle to the coordinates of the second position to perform the liquid infusion at the coordinates of the second position. Herein, the second position is determined based on the first position, and the coordinates of the second position are determined according to the coordinate origin. Moreover, when the remaining amount of liquid in the infusion apparatus is less than the threshold, the control device 105 sends third control information to the infusion actuator, such that the infusion actuator 109 withdraws the infusion needle from the second position to stop the liquid infusion. In one embodiment, when the liquid infusion is stopped, the infusion actuator 109 is reset to return to its original position.

In one embodiment, the infusion actuator 109 comprises an infusion needle driving device and a liquid control device (not shown). In particular, the infusion needle driving device is configured to adjust an angle and a direction of the infusion needle on the infusion actuator according to a tilt angle of the target object at the second position with respect to a horizontal line and a diameter size of the target object at the second position, and to control an end of the infusion needle to move to the coordinates of the second position for the liquid infusion. Moreover, when the remaining amount of liquid in the infusion apparatus is less than the threshold, the control device 105 sends the third control information to the infusion actuator 109, such that the infusion needle driving device of the infusion actuator 109 withdraws the infusion needle from the second position to stop the liquid infusion. The liquid control device is configured to control a speed and/or duration of the liquid infusion. Depending on the age, the sex, and the diameter size of the blood vessel of the person to be infused, the liquid control device may select a different liquid infusion speed and/or time to show the dynamic adjustment of the liquid infusion.

In one embodiment, the hemostasis actuator 110 is installed at an end of the robotic arm and is used to spray the cold analgesic sprays. In one embodiment, after the infusion actuator withdraws the infusion needle, the hemostasis actuator 110 sprays cold analgesic sprays at coordinates of a third position for hemostasis. Herein, the third position is determined based on the second position, and the coordinates of the third position are determined based on the coordinate origin. In one embodiment, after the cold analgesic sprays are sprayed, the imaging device 102 captures a third image of the object to be detected in a first state, and a determination of whether bleeding is stopped is made according to the third image. For example, when the analysis of the third shows that there is no spread of the bleeding point, it may be determined that the bleeding has been stopped. In addition, when it is determined that the bleeding has been stopped, the hemostasis actuator 110 resets to return to its original position. Subsequently, the control device 105 controls one or more robotic arms 108 to be withdrawn from the liquid input region.

In one embodiment, the intelligent infusion system 100 further comprises a tightening device (not shown in FIG. 1). In one embodiment, the tightening device is used to hold an upper arm to swell the blood vessels. Typically, when the liquid infusion is performed, in order to more clearly identify the blood vessels, a medical staff tightens the user's arm using a rubber band to swell the blood vessels. In one embodiment, the intelligent infusion system 100 of the present disclosure tightens the upper arm using the tightening device to swell the blood vessels. Typically, the tightening device may tighten the upper arm by using air pressure, bundling or the like.

Figure 2:
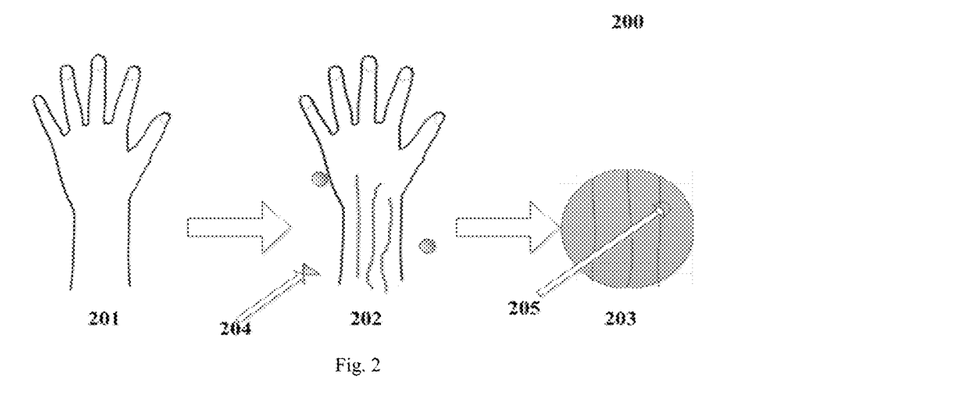
FIG. 2 shows a schematic diagram of a manner for determining a location according to an implementation of the present disclosure.

FIG. 2 shows a schematic diagram of a manner for determining a location according to an implementation of the present disclosure. As shown in FIG. 2, the imaging device 102 captures an image of a hand 201. According to an implementation of the present disclosure, the coordinate origin 204, the number of blood vessels, and information such as the position, the linear shape, the diameter size or the like of each blood vessel are determined in the image of hand 201, as shown in hand 202. The enlarged image 203 shows a partial enlarged image of the blood vessel in which the coordinates of the point where the needle 205 is inserted are (12.5, 10). FIG. 2 shows that the hand is in a relaxed state, and according to a preferred implementation of the present disclosure, in some cases the hand is in a tightened state (not shown). As described as above, the first state is the state in which the hand of the person to be infused is relaxed and laid flat, and the second state is the state in which the person to be infused clenches his fist. It is to be understood that when the object to be detected is in the first state and the second state, the blood vessel exhibits a different effect in the image due to shrinkage or relaxation. In the present disclosure, according to such case that the display effect is different, the image data of one or more blood vessels on the back of the hand is determined, that is, the image data of one or more objects to be processed is determined. Herein, the image data comprises information such as the position, the linear shape, the diameter size and the like of the blood vessel.

Figure 3:
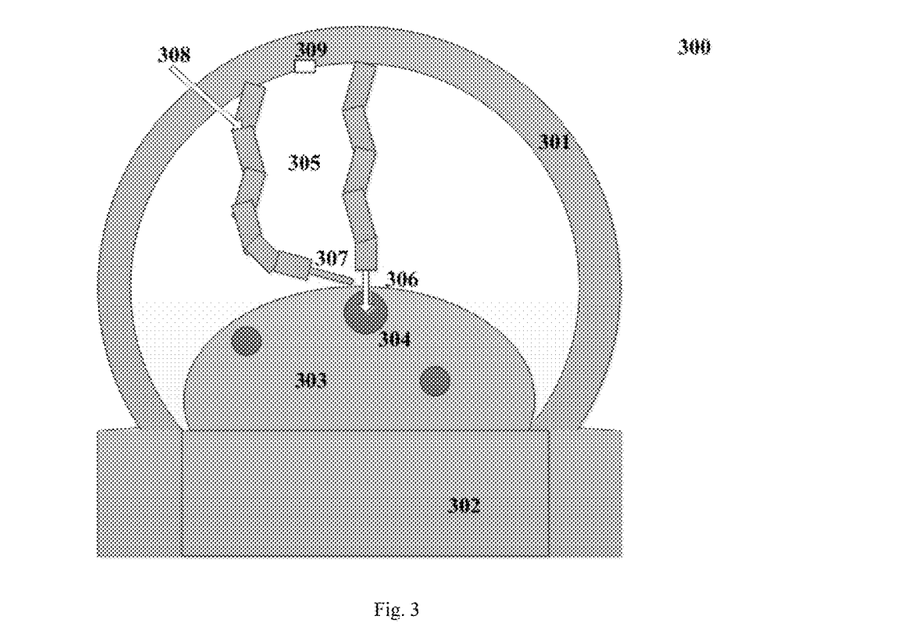
FIG. 3 illustrates a schematic structural view of an intelligent infusion apparatus according to an implementation of the present disclosure.

FIG. 3 illustrates a schematic structural view of an intelligent infusion apparatus 300 according to an implementation of the present disclosure. As shown in FIG. 3, the intelligent infusion apparatus 300 comprises a housing 301, a base 302, a robotic arm 305, an infusion actuator 306 and a hemostasis actuator 307. Herein, the infusion actuator 306 and the hemostasis actuator 307 are installed at an end of one of two robotic arms 305. In one embodiment, the housing 301 is used to accommodate the robotic arm 305 and a camera 309. As shown in FIG. 3, the robotic arm 305 is in a state of entering a liquid infusion region. When the robotic arm 305 is reset, it will return to the position perpendicular to the cross section of the housing 301. The base 302 is used to support the arms and accommodate circuits and equipments associated with the intelligent infusion. As shown in FIG. 3, the infusion actuator 306 at the end of the robotic arm 305 performs the liquid infusion on a blood vessel 304 in an arm 303, and the hemostasis actuator 307 at the end of the robotic arm 305 sprays cold analgesic sprays for hemostasis. In one embodiment, the cold analgesic sprays can be input from an input port 308.

Figure 4:
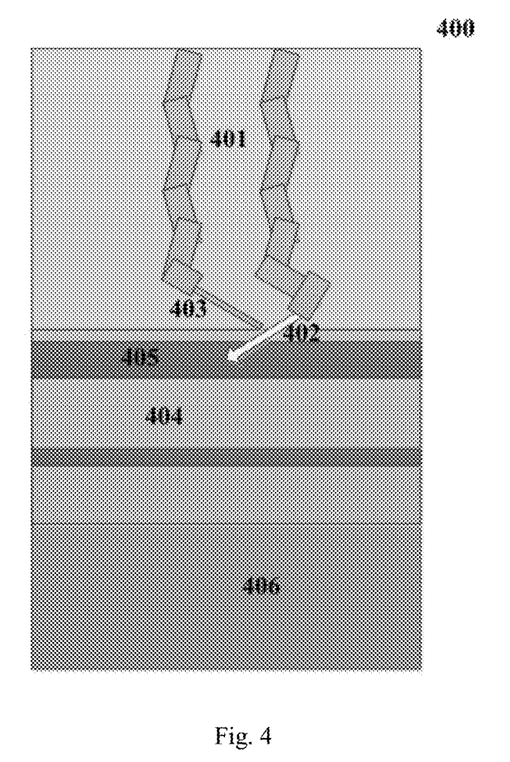
FIG. 4 illustrates another schematic structural view of an intelligent infusion apparatus according to an implementation of the present disclosure.

FIG. 4 illustrates another schematic structural view of an intelligent infusion apparatus 400 according to an implementation of the present disclosure. FIG. 4 is a side view of the intelligent infusion apparatus 300 shown in FIG. 3. Herein, the intelligent infusion apparatus 400 comprises a housing 407, a base 406, a robotic arm 401, an infusion actuator 402 and a hemostasis actuator 403.

Figure 5:
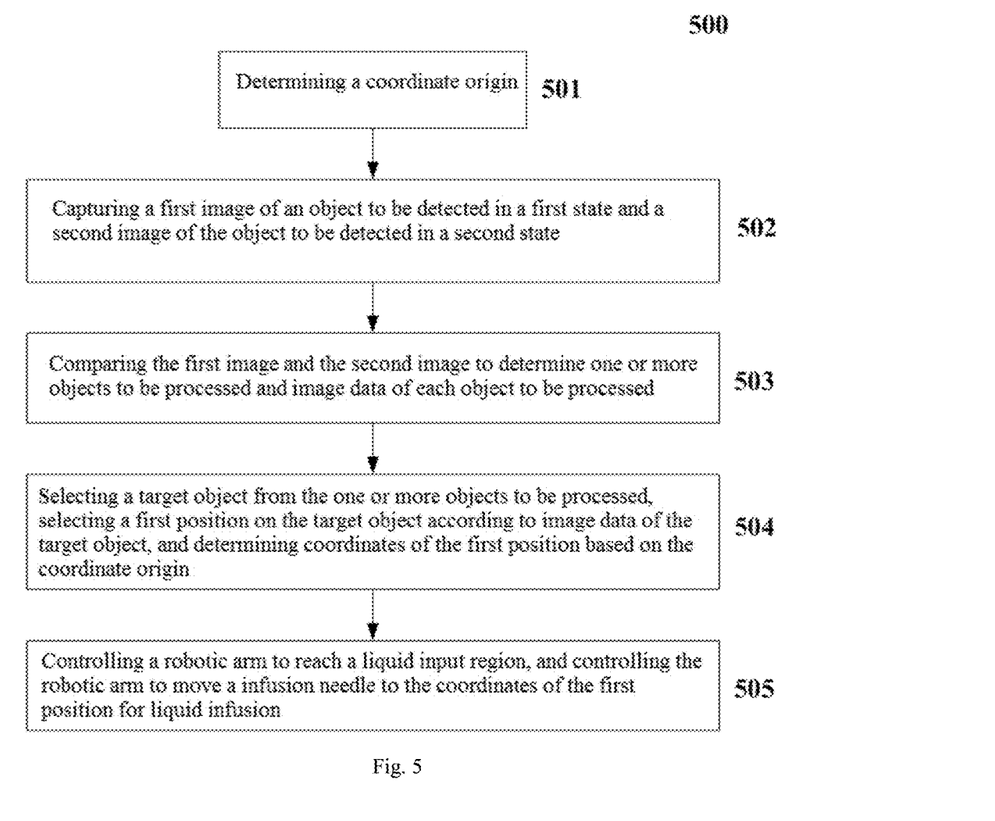
FIG. 5 shows a flow chart of a method of an infusion method using an intelligent infusion system according to an implementation of the present disclosure.

FIG. 5 shows a flow chart of a method of an infusion method 500 using an intelligent infusion system according to an implementation of the present disclosure. In one embodiment, the method 500 can compare and analyze image data according to an image processing technology to determine vascular distribution of a skin surface of a target object, and calculate information on a diameter size of a blood vessel according to the image data. Further, the method 500 sets the initial origin coordinates of the image data and confirms the optimal positional coordinates of the blood vessel for infusion based on the initial origin coordinates. Then, the method 500 adjusts an angle and a direction of an infusion needle being used for infusion according to the direction and the diameter size of the blood vessel, and then performs an action of inserting the needle accordingly. In one embodiment, the method 500 performs the above operations based on calculation and control of a central processing unit CPU.

In addition, the method 500 can monitor a remaining amount of liquid in the infusion apparatus in real time, and withdraw the infusion needle from the target object when it is determined that the remaining amount of liquid in the infusion apparatus is less than a threshold. In one embodiment, after the infusion needle is withdrawn from the target object, the method 500 determines the coordinates of the hemostatic position based on the coordinates of the position where the needle is inserted, and sprays cold analgesic sprays for hemostasis at the coordinates of the hemostatic position. When the image data is analyzed based on the image processing technique to determine that the bleeding is stopped, the method 500 performs a reset operation, for example, resetting the robotic arm.

In one embodiment, at step 501, a coordinate origin is determined. The coordinate origin is a reference for determining the coordinates of multiple locations used by a range of infusion treatments. For example, when one or more images of an object to be detected (e.g., a hand of a person who needs the infusion, usually the back of the hand) are acquired, the same coordinate origin is determined in one or more images. Also, the coordinate origin is used as a reference for determining a number of locations to be used later.

In one embodiment, at step 502, a first image of the object to be detected in a first state and a second image of the object to be detected in a second state are captured. For example, when determining one or more treatment objects (e.g., one or more blood vessels) on the object to be detected, a first image of the object to be detected in a first state and a second image of the object to be detected in a second state are captured. Usually, the first state is a relaxed state of the object to be detected, and the second state is a tightened state of the object to be detected. For example, the first state is the state in which the hand of the person to be infused is relaxed and laid flat, and the second state is the state in which the person to be infused clenches his fist. It is to be understood that when the object to be detected is in the first state and the second state, the blood vessel exhibits a different effect in the images due to shrinkage or relaxation. In the present disclosure, according to such case that the display effect is different, the image data of one or more blood vessels on the back of the hand is determined, that is, the image data of one or more objects to be processed is determined. Herein, the image data comprises information such as a position, a linear shape, a diameter size and the like of the blood vessel.

In one embodiment, the method 500 can also capture a magnified image. For example, when the liquid infusion is performed, it is usually necessary to obtain a magnified image at the input location to achieve a more accurate liquid infusion. In addition, after the liquid infusion is completed, it is usually necessary to perform an operation of stopping bleeding. In the operation of stopping bleeding, it is usually necessary to obtain a magnified image near the liquid infusion point to determine the sprayed location of the hemostatic drug and determine whether hemostasis is achieved after spraying the hemostatic drug.

In one embodiment, at step 503, the first image and the second image are compared to determine one or more objects to be processed and image data of each object to be processed. In particular, one or more objects to be processed are determined and a linear shape and a diameter size of each object to be processed are determined by comparing a color change of the first image and the second image. The number of the objects to be processed on the object to be detected is analyzed and determined based on the comparison of the first image and the second image. That is, the number of blood vessels on hand is determined. After one or more objects to be processed are determined, the image data for each object to be processed is also determined. Herein, the image data comprises information such as a position, a linear shape, a diameter size and the like of the blood vessel.

At step 504, a target object is selected from the one or more objects to be processed, a first position on the target object is selected according to image data of the target object, and coordinates of the first position are determined based on the coordinate origin. A target object is selected from the one or more objects to be processed according to image data of each object to be processed. That is, the blood vessel best suited for the liquid infusion from one or more vessels to be used as the target object is selected according to the information such as a position, a linear shape, a diameter size and the like of each blood vessel. Then, a first position is selected on the target object based on the image data of the target object, and the coordinates of the first position are determined based on the coordinate origin. That is, after the target object is determined, the first position best suitable for the liquid infusion on the blood vessel is further selected according to the information such as the linear shape, the diameter size and the like of the blood vessel.

In one embodiment, the method 500 further comprises calculating a second position based on the first position. According to a preferred implementation of the present disclosure, when the liquid infusion is performed, the infusion needle is first placed on the first position. Herein, the first position is at a certain distance from the point where the infusion needle is being used for the liquid infusion, and the second position is a precise position where the infusion needle being used for the liquid infusion contacts the skin. Generally, when the liquid infusion is performed, the infusion needle is firstly moved to the first position, and the infusion needle is then moved to the second position near the first position by a more sophisticated instrument to carry out the liquid infusion at the second position. In one embodiment, the method 500 further comprises calculating a third position based on the second position. Herein, the third position is a center position where the hemostatic actuator (described later) sprays the cold analgesic sprays after the liquid infusion is completed. That is, the cold analgesic sprays are sprayed at the third position as a center.

At step 505, a robotic arm is controlled to reach a liquid input region, and the robotic arm is controlled to move a infusion needle to the coordinates of the first position for liquid infusion. When the liquid infusion is to be performed, first control information is generated, and the first control information is sent to the robotic arm, such that the robotic arm reaches the liquid input region. Herein, after the robotic arm reaches the liquid input region, the liquid infusion and hemostasis functions can be done respectively or separately, as described in detail below.

In one embodiment, the method 500 further comprises detecting a remaining amount of liquid in an infusion apparatus. Typically, when the remaining amount of liquid in the infusion apparatus is below a threshold, for example less than 5 ml, the liquid infusion should be stopped and the infusion needle should be withdrawn from the target object. It is to be understood that one skilled in the art may set the threshold to any reasonable value. In addition, the method 500 further comprises detecting an infusion flow rate, a blood flow rate, a heart frequency and other parameters. In one embodiment, the method 500 further comprises displaying one or more of the remaining amount of liquid in the infusion apparatus, the infusion flow rate, the blood flow rate and the heart frequency, such that the user can know about the relevant information in time.

In one embodiment, the method 500 further comprises generating second control information and sending the second control information to an infusion actuator installed at an end of the robotic arm. The infusion actuator moves the infusion needle to the coordinates of the second position. Herein, the second position is determined based on the first position, and the coordinates of the second position is determined based on the coordinate origin.

In one embodiment, the method 500 further comprises adjusting an angle and a direction of the infusion needle on the infusion actuator according to a tilt angle of the target object at the second position with respect to a horizontal line and a diameter size of the target object at the second position, and controlling an end of the infusion needle to move to the coordinates of the second position for the liquid infusion.

In one embodiment, the method 500 further comprises: when the remaining amount of liquid in the infusion apparatus is less than the threshold, sending third control information to the infusion actuator, such that the infusion actuator withdraws the infusion needle from the second position. In one embodiment, the method 500 further comprises: after the infusion actuator withdraws the infusion needle, spraying cold analgesic sprays at coordinates of a third position, wherein the third position is determined based on the second position, and the coordinates of the third position are determined based on the coordinate origin; or after the infusion actuator withdraws the infusion needle, spraying the cold analgesic sprays at coordinates of a third position by using a hemostasis actuator installed at an end of another robotic arm, wherein the third position is determined based on the second position, and the coordinates of the third position are determined based on the coordinate origin.

In one embodiment, the method 500 further comprises: after the cold analgesic sprays are sprayed, capturing a third image of the object to be detected in a first state by using the imaging device, and determining whether an operation is completed according to the third image. Herein, the robotic arm is controlled to leave the liquid input region when it is determined that the operation is completed.

In one embodiment, the method 500 further comprises holding an upper arm by using a tightening device to swell the blood vessels. Typically, when the liquid infusion is performed, in order to more clearly identify the blood vessels, a medical staff tightens the user's arm using a rubber band to swell the blood vessels. In one embodiment, the method 500 of the present disclosure tightens the upper arm by using the tightening device to swell the blood vessels. Typically, the method 500 may tighten the upper arm by using air pressure, bundling or the like.

The present disclosure has been described by reference to several implementations. However, as is well known to those skilled in the art, other embodiments as disclosed above in the present disclosure are equally defined within the scope of the present disclosure, as defined in the appended claims.

In general, all terms used in the claims are construed in accordance with their ordinary meaning in the technical field unless they are otherwise expressly defined herein. All references to "one/the/such (device, component, etc.)" are expressly interpreted as at least one instance of the device, component, etc., unless otherwise explicitly stated. The steps of any method disclosed herein do not necessarily operate in the disclosed accurate order, unless explicitly stated.

What is claimed is:

1. An intelligent infusion system, comprising:
   a positioning device configured to determine a coordinate origin;
   an imaging device configured to capture a first image of an object to be detected in a first state and a second image of the object to be detected in a second state;
   a processing device configured to compare the first image and the second image to determine one or more objects to be processed and image data of each object to be processed;
   a calculation device configured to select a target object from the one or more objects to be processed, select a first position on the target object according to image data of the target object and determine coordinates of the first position based on the coordinate origin; and
   a control device configured to control a robotic arm to reach a liquid input region and control the robotic arm to move a infusion needle to the coordinates of the first position for liquid infusion.

2. The intelligent infusion system of claim 1, wherein the control device generates first control information and sends the first control information to the robotic arm, such that the robotic arm reaches the liquid input region.

3. The intelligent infusion system of claim 2, wherein the control device generates second control information and sends the second control information to an infusion actuator installed at an end of the robotic arm, the infusion needle is installed at an end of the infusion actuator, and when the infusion actuator receives the second control information, the infusion actuator moves the infusion needle to coordinates of a second position, and performs the liquid infusion at the coordinates of the second position.

4. The intelligent infusion system of claim 3, wherein the infusion actuator comprises an infusion needle driving device and a liquid control device.

5. The intelligent infusion system of claim 4, wherein the infusion needle driving device is configured to adjust an angle and a direction of the infusion needle on the infusion actuator according to an extension direction of the target object at the second position and a diameter size of the target object at the second position, and to control an end of the infusion needle to move to the coordinates of the second position for the liquid infusion.

6. The intelligent infusion system of claim 4, wherein the liquid control device is configured to control a speed and/or duration of the liquid infusion.

7. The intelligent infusion system of claim 3 further comprising a hemostasis actuator installed at the end of the robotic arm, and after the infusion actuator withdraws the infusion needle, the hemostasis actuator sprays cold analgesic sprays at coordinates of a third position for hemostasis.

8. The intelligent infusion system of claim 3 further comprising another robotic arm, the hemostasis actuator is installed at an end of said another robotic arm, and after the infusion actuator withdraws the infusion needle, the hemostasis actuator sprays cold analgesic sprays at coordinates of a third position for hemostasis.

9. The intelligent infusion system of claim 7, wherein after the cold analgesic sprays are sprayed, the imaging device captures a third image of the object to be detected in the first state, and a determination of whether bleeding is stopped is made according to the third image.

10. The intelligent infusion system of claim 9, wherein when it is determined that the bleeding is stopped, the control device controls the robotic arm to leave the liquid input region.

11. An infusion method using an intelligent infusion system, comprising:
   determining a coordinate origin;
   capturing a first image of an object to be detected in a first state and a second image of the object to be detected in a second state;
   comparing the first image and the second image to determine one or more objects to be processed and image data of each object to be processed;
   selecting a target object from the one or more objects to be processed, selecting a first position on the target object according to image data of the target object, and determining coordinates of the first position based on the coordinate origin; and
   controlling a robotic arm to reach a liquid input region, and controlling the robotic arm to move a infusion needle to the coordinates of the first position for liquid infusion.

12. The infusion method of claim 11 further comprising generating first control information and sending the first control information to the robotic arm, such that the robotic arm reaches the liquid input region.

13. The infusion method of claim 12 further comprising generating second control information and sending the second control information to an infusion actuator installed at an end of the robotic arm, and when the infusion actuator receives the second control information, the infusion actuator moves the infusion needle installed at the end thereof to coordinates of a second position.

14. The infusion method of claim 13 further comprising adjusting an angle and a direction of the infusion needle on the infusion actuator according to an extension direction of the target object at the second position and a diameter size of the target object at the second position, and controlling an end of the infusion needle to move to the coordinates of the second position.

15. The infusion method of claim 13 further comprising spraying cold analgesic sprays at coordinates of a third position after the infusion actuator withdraws the infusion needle.

16. The infusion method of claim 13 further comprising spraying cold analgesic sprays at coordinates of the third position by using a hemostasis actuator installed at an end of another robotic arm, after the infusion actuator withdraws the infusion needle.

17. The infusion method of claim 15 further comprising capturing a third image of the object to be detected in a first state by using the imaging device and determining whether an operation is completed according to the third image, after the sprays are sprayed.

18. The infusion method of claim 17 further comprising controlling the robotic arm to leave the liquid input region when it is determined that the operation is completed.

19. The infusion method of claim 11, wherein the step of comparing the first image and the second image to determine one or more objects to be processed and image data of each object to be processed comprises:
   determine one or more objects to be processed and determine a linear shape and a diameter size of each object to be processed by comparing a color change of the first image and the second image.

20. The infusion method of claim 11 further comprising acting on the object to be detected such that an image of the processing object is clearer.

* * * * *